United States Patent [19]

Nutt

[11] 4,374,060

[45] Feb. 15, 1983

[54] PROCESS FOR THE PREPARATION OF CYCLIC HEXAPEPTIDE

[75] Inventor: Ruth F. Nutt, Green Lane, Pa.

[73] Assignee: Merck & Co., Inc., Rahway, N.J.

[21] Appl. No.: 283,404

[22] Filed: Jul. 15, 1981

[51] Int. Cl.³ .......................................... C07C 103/52
[52] U.S. Cl. ........................ 260/112.5 R; 260/112.5 S
[58] Field of Search .................. 260/112.5 R, 112.5 S

[56] References Cited

U.S. PATENT DOCUMENTS 4,102,877  7/1978  Nutt ............................. 260/112.5 R
4,108,987  8/1978  Veber et al. ................. 260/112.5 R
4,285,857  8/1981  Chipens et al. ............. 260/112.5 R

OTHER PUBLICATIONS

European Published Patent Specification Appln. No. 80303826.4, Publication NO. 0029310–Mar. 5, 1980.

Chem. Abstr., vol. 66, (1967), 22714a.
Chem. Abstr., vol. 83, (1975), 205804a.
Chem. Abstr., vol. 74, (1971), 12350e.
Chem. Abstr., vol. 73, (1970), 66888j.

*Primary Examiner*—Delbert R. Phillips
*Attorney, Agent, or Firm*—David L. Rose; Mario A. Monaco

[57] ABSTRACT

There is disclosed a process for preparing a cyclic hexapeptide somatostatin analog, specifically cyclo (D-Trp-Lys-Val-Phe-N-Me-Ala-Tyr). The cyclic hexapeptide is synthesized in large quantities in a solution synthesis procedure. However, because of the unexpectedly rapid cyclization rate of this compound, conditions have been developed such that a much more concentrated solution, and thus smaller volumes of the reaction medium, may be employed than would be expected.

4 Claims, No Drawings

PROCESS FOR THE PREPARATION OF CYCLIC HEXAPEPTIDE

BACKGROUND OF THE INVENTION

The cyclic hexapeptide somatostatin analog cyclo-(D-Trp-Lys-Val-Phe-N-Me-Ala-Tyr) is synthesized in small quantities by cyclizing the corresponding linear peptide hydrazide. This process generally requires that the cyclization medium be maintained in a dilute condition to prevent dimerization. When large quantities of cyclic hexapeptide are required, very large reaction vessels would be necessary to maintain the proper level of dilution. The process of the instant invention provides for larger quantities of the cyclic hexapeptide, but allows for a much more concentrated reaction mixture, thus the anticiptated large quantities of solvent are avoided. This results in a considerable cost saving when large quantities of the product are being prepared.

SUMMARY OF THE INVENTION

This invention is concerned with the cyclization of the cyclic hexapeptide somatostatin analog cyclo-(D-Trp-Lys-Val-Phe-N-Me-Ala-Tyr) using solution synthesis techniques wherein the unexpectedly high reactivity of the linear peptide is such that more concentrated reaction solutions may be utilized than would be expected. Thus, it is an object of this invention to describe such a cyclization process. It is a further object to describe the various linear precursors of the cyclic hexapeptide. A still further object is to describe one possible process for the preparation of such linear precursors. Further objects will become apparent from a reading of the following description.

DESCRIPTION OF THE INVENTION

The cyclic hexapeptide cyclo-(D-Trp-Lys-Val-Phe-N-Me-Ala-Tyr) is a somatostatin analog utilizing 6 of the 14 positions of the original somatostatin molecule. The compound inhibits the release of glucagon, growth hormone and insulin. The compound has a higher level of activity than somatostatin and a longer duration of activity. Thus the compound has a more selective biological activity than somatostatin. The compound may thus be useful for the treatment of acromegaly, diabetes and diabetic retinopathy.

In the instant application several abbreviated designations are used for the amino acid components, certain preferred protecting groups, reagents and solvents. The meanings of such abbreviated designations are given in Table I.

TABLE I

| Abbreviated Designation | |
|---|---|
| | Amino Acid |
| Lys | lysine |
| Phe | phenylalanine |
| Trp | tryptophan |
| Thr | threonine |
| Aha | 7-aminoheptanoic acid |
| Tyr | tyrosine |
| Val | valine |
| Abu | α-aminobutyric acid |
| Ser | serine |
| Asn | asparagine |
| Pro | proline |
| Asu | amino-suberic acid |
| Cys | cysteine |
| | Protecting Groups |
| INOC | isonicotinyloxycarbonyl |
| BOC | tert-butyloxycarbonyl |
| OMe | methyl ester |
| Bu | tert-butyl |
| Cbz | benzyloxycarbonyl |
| Bzl | benzyl |
| 2-Cl—Cbz | 2-chlorobenzyloxycarbonyl |
| Acm | acetamidomethyl |
| Me | methyl |
| | Activating Groups |
| ONp | p-nitrophenyl ester |
| HSE | N—hydroxysuccinimide ester |
| HBT | 1-hydroxybenzotriazole |
| | Activating Agents |
| DCCI | dicyclohexylcarbodiimide |
| | Reagents |
| TFA | trifluoroacetic acid |
| TEA | triethylamine |
| DIPEA | diisopropylethylamine |
| EDT | ethanedithiol |
| DPPA | diphenylphosphoryl azide |
| SDPP | N—succinimidyl-diphenylphosphate |
| | Solvents |
| EPAW | ethyl acetate-pyridine-acetic acid-water |
| BAW | butanol-acetic acid-water |
| CMW | chloroform-methanol-water |
| DMF | dimethylformamide |
| THF | tetrahydrofuran |

The instant invention specifically refers to the cyclization of a linear hexapeptide to the above cyclic hexapeptide. It will be appreciated that many different linear peptides may be employed to prepare the one cyclic peptide, since once the linear compound is cyclized, there is no way to determine the linear compound from which it was derived. Of the 6 possible linear peptides which can be employed to prepare the cyclic hexapeptide 5 have been found to be sufficiently reactive to be able to take advantage of the higher concentration used in the instant process. Those linear hexapeptides are:

H-D-Trp-Lys-Val-Phe-N-Me-Ala-Tyr-OH
H-Tyr-D-Trp-Lys-Val-Phe-N-Me-Ala-OH
H-Phe-N-Me-Ala-Tyr-D-Trp-Lys-Val-OH
H-Val-Phe-N-Me-Ala-Tyr-D-Trp-Lys-OH
H-Lys-Val-Phe-N-Me-Ala-Tyr-D-Trp-OH

The preferred linear peptide is the first of the above listed group of peptides.

The cyclization of the above peptides is carried out with the Lysine side chain protected, preferably with a benzyloxycarbonyl (Cbz) protecting group although other protecting groups known to those skilled in the peptide art may also be used. Examples of such other protecting groups are: tert-butyloxycarbonyl, 9-fluorenylmethyloxycarbonyl, p-toluenesulfonyl and aromatic substituted forms of benzenesulfonyl, acetyl and halogenated acetyls, isonicotinyloxycarbonyl, phthalimide, 4,5-diphenyl-4-oxazolin-2-one, tritylsulfenyl, and aryl sulfenyl, and salts.

The foregoing protecting groups are used to protect the Lys amino acid, and also may be used to protect other functions on the peptide chain during the course of the reaction sequence. In particular, the tert-butyloxycarbonyl (BOC) is used to protect the N-terminal hydrogen of the reacting amino acid during the mixed anhydride coupling reactions.

The unique characteristics of the instant linear peptides is that the cyclization reaction occurs with more rapid reaction kinetics than is observed in many peptide cyclization reactions. As a result the reaction can be carried out in a much more concentrated state than is employed in normal peptide cyclizations. As a result, the reaction volume used for a given amount of linear peptide is greatly reduced. Consequently, larger quantities of the cyclic hexapeptide may be produced without resorting the unwieldy reaction volumes. The reaction is generally carried out at a concentration of from 0.5 to 0.001 molar concentration. Preferably concentrations of about 0.008 molar are employed. This is about from 10 to 100 times more concentrated than is generally employed for similar peptide cyclization reactions.

The reaction is carried out in a solvent of N,N-dimethylformamide, or dimethylsulfoxide, in the presence of a base such as a tertiary amine or an inorganc base and a cyclizing agent. The tertiary amine is preferably triethylamine, and the inorganic base is preferably sodium bicarbonate. Sodium bicarbonate, employed in excess, is the most preferred base. The cyclization agents are selected from the following:

Diphenylphosphoryl azide
N-succinimidyl diphenylphosphate
Diphenylphosphoryl cyanidate
Dicyclohexylcarbodiimide
(including conditions where additive nucleophile catalysts such as 1-hydroxybenzotriazole and N-hydroxysuccinimide are present)
Isobutylchloroformate and other alkyl chloroformates
Ethoxy acetylene
N-ethyl-5-phenylisoxazolium-3'-sulfonate
1-ethoxycarbonyl-2-ethoxy-1,2-dihydroquinoline
triphenylphosphine with dialkyl disulfides.

The preferred cyclization reagents are diphenylphosphoryl azide (DPPA) and N-succinimidyl diphenylphosphate (SDPP). DPPA is most preferred.

The cyclization is carried out in N,N-dimethylformamide from $-30°$ to $+25°$ C. and the reaction is complete in from 1 to 50 hours.

The solvent is evaporated, and the product isolated using techniques known to those skilled in the art.

The linear peptides which are cyclized using the above process may be prepared using any of the procedures commonly used to synthesize linear peptides. The instant process is not dependent upon any particular synthetic scheme as a source of the starting peptide.

One process which has proven itself to be satisfactory however is outlined in the following reaction scheme. This reaction scheme prepares one of the linear peptides which may be used in the cyclization step viz H-D-Trp-Lys-Val-Phe-N-Me-Ala-Tyr-OH. The linear peptide is suitably protected to prevent any unwanted side reactions.

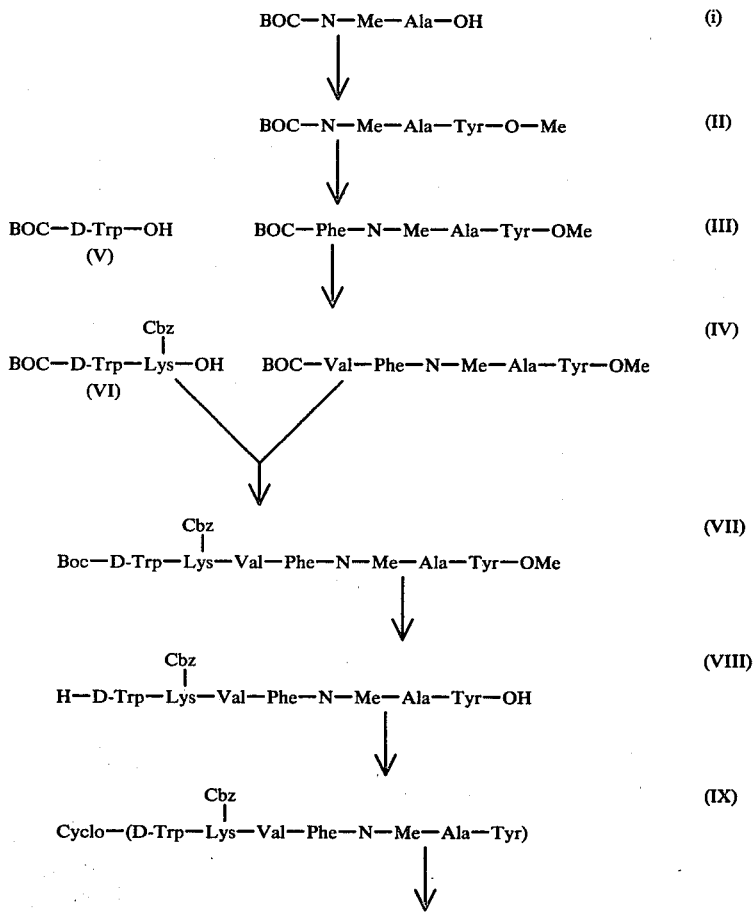

Cyclo—(D-Trp—Lys—Val—Phe—N—Me—Ala—Tyr)   (X)

In the foregoing reaction scheme the coupling reaction for the preparation of compounds II, III, IV, VI, and VII are carried out using the mixed anhydride method. Thus the processes wherein an amino acid or peptide is added to an existing amino acid or peptide all involve basically the same chemistry. The mixed anhydride is first formed by reacting a protected amino acid or peptide with isobutyl chloroformate in the presence of an equimolar amount of base such as N-methyl morpholine. The reaction is preferably carried out at from −5° to 0° C. and is complete in from 5 to 30 minutes. The amino acid or peptide to be coupled, which is also suitably protected, is then added and the reaction mixture stirred at −10° to 0° C. from 1 to 5 hours. The reaction produces a loss of carbon dioxide and isobutylalcohol and the product is isolated using techniques known to those skilled in the art.

Prior to the mixed anhydride coupling reaction the substrate must be selectively deblocked to permit the reaction to proceed at the desired reaction site. In the case of compounds II, III and IV this involves removing a BOC protecting group. The BOC-protected peptide is removed with acid catalysis using hydrogen chloride gas or trifluoroacetic acid. In deblocking compound IV trifluoroacetic acid is preferred and in deblocking the others, hydrogen chloride gas is preferred. A saturated solution, or a solution with as much as 15% by weight of the hydrogen chloride gas in ethyl acetate, dioxane, tetrahydrofuran and the like at from −50° to +15° C. and stirring for from 2 minutes to 90 minutes is generally employed. Ethyl acetate is the preferred solvent. It is preferred to carry out the reaction at about −10° C. When a trifluoroacetic acid solution is used a 1:1 mixture in methylene chloride is generally preferred, however, a 100% trifluoroacetic acid solution is also often successful. The reaction is carried out at from −30° C. to room temperature for from 5 minutes to 3 hours. It is preferred to carry out the reaction at about −10° C.

If Trp is present on the peptide being formed or reacted, it is advisable to include at least an equimolar amount of a scavenger such as ethanedithiol or other strong nucleophile to prevent any side reactions on the Trp moiety.

The preparation of compound VIII involves a saponification step as well as the removal of the BOC protecting group. This is to remove the C-terminal methyl ester to prepare the peptide for cyclization. The ester is treated with sodium hydroxide or other strong hydroxide base. The solvent is a mixture of water and a water miscible organic solvent which is at least 50% water. Tetrahydrofuran, dioxane, methanol, ethanol and the like are acceptable. Tetrahydrofuran is preferred. The pH is maintained at from 9 to 12.5, preferably at a higher pH within the range. The reaction should not be allowed to go beyond a pH of 12.5 however since racemization can occur. The reaction is usually carried out at room temperature for from 30 minutes to 12 hours.

The compound thus prepared (VIII) is then cyclized as described above.

To prepare the final product the final protecting group on the Lys must be removed. Usually the Cbz group is employed and thus is removed most effectively using catalytic transfer hydrogenolysis. The reducing hydrogen is generated in this case from formic acid, generally present as a formic acid solution or ammonium formate, and palladium catalyst on a carbon support. The palladium is generally present on the carbon at up to 10% by weight and the entire catalyst is employed at from 5 to 100% of the weight of the peptide. Other hydrogen generator compounds such as 1,4-cyclohexadiene or cyclohexane may also be employed but formic acid is preferred. The reaction is carried out in an alcohol solvent such as methanol or ethanol at from 0° to 50° C. however room temperature is preferred. The reaction is generally complete in from 30 minutes to 24 hours. The product is isolated and purified using techniques known to those skilled in the art.

An alternate approach to the dipeptide VI is outlined in the following reaction scheme:

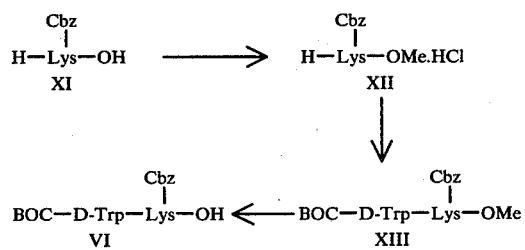

The protected lysine (XI) is converted to the methyl ester hydrochloride (XII) using boron trifluoride etherate in methanol with heating at from 30° to 65° C. for from 10 to 40 hours. Compound XII is then coupled with BOC protected Trp using the mixed anhydride process discussed above and the methyl ester is saponified using the sponification process discussed for the compound VII→VIII processes.

The following examples are presented in order that the invention might be more fully understood. They are not to be construed as limitative of the invention.

EXAMPLE 1

BOC-N-Me-Ala-Tyr-OME 1 liter of ethyl acetate under nitrogen is cooled to between −5° and 0° C. and isobutyl chloroformate (37.6 ml, 290 mmole) is added followed by N-methylmorpholine (31.9 ml, 290 mmole). A sticky white solid forms and after 10 minutes BOC-N-methylalanine (58.9 grams, 290 mmoles) is added. A more granular solid forms and after 20 minutes tyrosine methylesterhydrochloride (57.93 grams, 250 mmoles) is added. Additional N-methylmorpholine (27.9 ml, 250 mmoles) is then added to obtain a pH of about 8. After 2.5 hours of stirring the mixture is washed three times with 500 ml of 1 N sodium bicarbonate and three times with 500 ml of 0.5 molar citric acid and dried over sodium sulfate. The reaction mixture is concentrated in vacuo affording the following crops of crystalline materials:

Crop A—34.63 grams, melting point 124°–125° C.
Crop B—31.56 grams, melting point 116°–123° C.
Crop C—16.22 grams, melting point 122°–123.5° C.

EXAMPLE 2

Deblocking of BOC-N-Me-Ala-Tyr-OMe

A mixture of 82.24 grams (216 mmoles) of BOC-N-Me-Ala-Tyr-OMe and 500 ml of ethyl acetate is cooled to −10° C. under nitrogen. Hydrogen chloride gas is bubbled into the mixture and after 5 minutes a saturated solution is obtained and the temperature raised to 9° C. A solid material starts separating from the mixture and the hydrogen chloride gas is bubbled for an additional 10 minutes. As the temperature is brought to −7° C. nitrogen gas is then bubbled into the reaction mixture for 25 minutes and the cooling bath removed. Ether (300 ml) is added and the reaction mixture filtered and washed with a 1:1 mixture of ether and hexane (200 ml) followed by 200 ml of hexane. The filtered solid is dried in vacuo at room temperature in the presence of phosphorous pentoxide. The dried product weighs 68.3 grams, and has a melting point of 140°–142° C.

EXAMPLE 3

BOC-Phe-N-Me-Ala-Tyr-OMe

The procedure of Example 1 is followed using 1 liter of ethylacetate, 30.68 ml of isobutyl chloroformate, 26.00 ml of N-methylmorpholine, 62.72 grams of BOC-phenylalanine and 68 grams of N-Me-Ala-Tyr-OMe affording 3 crops of product as follows:
Crop A—55.78 grams, melting point 145°–146.5° C.
Crop B—5.92 grams, melting point 145°–146° C.
Crop C—12.17 grams, melting point 145°–146° C.

EXAMPLE 4

Deblocking of BOC-Phe-N-Me-Ala-Tyr-OMe

Following the procedure of Example 2 using 73.37 grams of BOC-Phe-N-Me-Ala-Tyr-OMe in 500 ml of ethylacetate and hydrogen chloride gas there is obtained 3 crops of "Phe-N-Me-Ala-Tyr-OMe" as follows:
Crop A—58.21 grams
Crop B—6.05 grams
Crop C—2.47 grams

EXAMPLE 5

BOC-Val-Phe-N-Me-Ala-Tyr-OMe

Following the procedure of Example 1 using 480 ml of ethylacetate, 19.84 ml of isobutyl chloroformate, 16.81 ml of N-methylmorpholine, 33.21 grams of BOC-Val and the product from Example 4 with an additional 10 ml of N-methylmorpholine there is obtained 66.66 grams of "Val-Phe-N-Me-Ala-Tyr-OMe."

EXAMPLE 6

Deblocking of BOC-Val-Phe-N-Me-Ala-Tyr-OMe

A suspension of 41.6 g (664 mmoles) of BOC-Val-Phe-NMe-Dla-Tyr-OMe in 190 ml of methylenechloride is stirred under a slow stream of nitrogen for 10 minutes and cooled to 5°–10° C. The reaction mixture is then treated with 190 ml of 100% TFA and dissolution was complete in less than 1 minute. The mixture is stirred at 5° C. (ice) for 35 minutes. The solution is then poured rapidly into 1500 ml of ether briskly stirred and pre-cooled to −20° C. A precipitate immediately forms. 50 Ml of methylenechloride is used to rinse out the reaction flask. 1600 Ml of 30°–60° petroleum ether is added after 5 minutes and stirred for 5 minutes more. The mixture stands for 30 minutes at 0° C. to complete precipitation. The product is isolated by filtration, washing 3 times with 600 ml portions of 50% ether/petroleum ether, and dried in vacuo affording 40.3 g of Val-Phe-NMeAla-Tyr-OMe which is characterized by elemental analysis, peptide analysis and HPLC analysis.

EXAMPLE 7

BOC-D-Trp-Cbz-Lys 1.52 grams of BOC-D-Trp is dissolved in 20 ml of tetrahydrofuran and cooled to −5° C. and 0.7 ml of TEA is added followed by 0.65 ml of isobutyl chloroformate, 1.40 grams of Cbz-Lys which had been previously dissolved in 10 ml of 0.5 normal sodium hydroxide is added whereupon an immediate precipitate is formed. An additional 27 ml of tetrahydrofuran and 5 ml of water is added to the reaction mixture. Additional TEA is added to maintain the pH at from 7.6 to 7.8. The reaction mixture is maintained at 5° C. overnight. 100 ml of water is added and the pH lowered to 2.7 using 10 to 15 percent hydrochloric acid. The solution is then extracted 3 times with 30 ml of ethylacetate. The ethylacetate is dried over sodium sulfate and evaporated to dryness in vacuo affording approximately 3 grams of material. This material is placed on a column containing 500 ml of silica gel and eluted with a solvent system consisting of an 85:15:1.5 mixture by volume of chloroform, methanol and concentrated aqueous ammonia. 25 Ml fractions are collected and fractions 64 to 105 are combined as the center-cut with fractions 42 to 63 and 106 to 114 combined as the sidecuts. The solvent is removed affording 0.821 grams for the centercut and 1.2574 grams for the combined sidecuts. The centercut is crystallized by dissolving in carbon tetrachloride and allowing the carbon tetrachloride to evaporate while adding a methylene chloride/ether mixture. This procedure is also used on the combined sidecuts affording 0.5111 grams and 0.6666 grams of "BOC-D-Trp-Cbz-Lys" respectively.

EXAMPLE 8

Coupling of $$\text{BOC—D-Trp—} \overset{\overset{\text{Cbz}}{|}}{\text{Lys}} \text{—OH}$$

Dipeptide and the Val-Phe-N-Me-Ala-Tyr-OMe Tetrapeptide 43.3 mg of BOC-D-Trp-(Cbz)-Lys-OH is dissolved in 750 ml of ethylacetate, 8.2 ml of N-methylmorpholine is added and the reaction mixture cooled to −5° C. 9.7 Ml of isobutyl chloroformate is added and the reaction mixture stirred for 12 minutes. 45 G of the trifluoroacetate of Val-Phe-N-Me-Ala-Tyr-OMe is added along with 6.5 ml of N-methylmorpholine in 150 ml of DMF. Further additions of N-methylmorpholine (4.2 ml) are made as required to maintain the pH at approximately 7.5. The reaction mixture is stirred for 2 hours at −5° C. and 120 ml of water is added. After standing overnight, the ethyl acetate solution is washed with 500 ml portions of water, 0.5 M citric acid, water, 0.5 M potassium bicarbonate, water (twice), and saturated sodium chloride. The ethyl acetate layer is dried over sodium sulfate, filtered and evaporated to dryness in vacuo affording 78.1 grams of BOC-D-Trp-(Cbz)-Lys Val-Phe-N-Me-Ala-Tyr-OMe.

EXAMPLE 9

Deblocking of BOC-D-Trp-Cbz-Lys-Val-Phe-N-Me-Ala-Tyr-Ome

A sample of 6.3 g (5.86 mmoles) of crude Boc-D-Trp-(Cbz)Lys-Val-Phe-N-MeAla-Tyr-OMe is dissolved in 60 ml of peroxide-free THF, and 30 ml of water is added with stirring. Then 2.5 N sodium hydroxide is added (using pH meter with electrode calibrated to 1:2 pH 10.00 buffer standard—THF) sufficient to give a pH of 10.75, maintaining the pH for ½ hour at pH 10.5–11.0. A slow drop in pH is noted and brought to pH 11.3 after 1 hour. The pH is kept at 11.0–11.5 for another B 2¾ hours and pH 12.0 for 3 more hours. The pH is reduced to pH 6.5 using 2.5 N HCl, and allowed to stand overnight.

The pH is again adjusted to a pH of less than 3 and evaporated at 35°–40° C. to a gummy paste, to which is added 200 ml of ethylacetate and 80 ml of of water. The layers are separated and the aqueous layer treated with less than 1 ml of 2.5 HCl to give pH 3. Ethylacetate is added and the layers separated. The organic layer is washed with 80 ml of water, 80 ml of 50% saturated sodium chloride solution and dried over anhydrous magnesium sulfate. The solution is filtered and evaporated to an oil. The oil is treated with 15 ml of methylene chloride and 30 ml of ethylacetate to give a smooth pasty solid. Then 20 ml of ethylacetate and 35 ml of methylene chloride is added. The mixture stands for 2 hours at 20° C. then 1 hour at 0° C. 40 Ml of cold 50% ethylacetate-methylenechloride is added to loosen the mixture. The mixture is filtered while cold and the filter cake is washed with 40 ml of cold 50% ethylacetate-methylenechloride and dried in vacuo affording 4.07 g of BOC-D-Trp-(Cbz)-Lys-Val-Phe-N-Me-Ala-tyr-OH m.p. 115°–135° (dec.). A second crop affords 0.81 g.

EXAMPLE 10

H-D-Trp-Cbz-Lys-Val-Phe-N-Me-Ala-Tyr-OH

The product of Example 9, 4.81 g (4.53 mmoles), is dissolved in 100 ml of ethylacetate and cooled to −50° C. under a slow stream of nitrogen and treated with HCl gas at such a rate that rapid warming occurs, and saturation is reached after B 8–10 minutes (temp. −15° C.). The reaction is maintained at saturation at −10°/−15° C. for 15 minutes and purged with nitrogen for 30 minutes (temp. dropped to −40° C. in 5 minutes, warming slowly to −20° C.). 100 Ml of ether is added after 35 minutes to give a precipitate which is triturated after 5 minutes, filtered and the solid material washed three times with 50 ml portions of ether. The solid material are dried in vacuo affording 3.60 g of H-D-Trp-Cbz-Lys-Val-Phe-N-Me-Ala-Tyr-OH.

A further solid precipitates from the filtrate to which is added 50 ml of ether, allowed to stand for 15 minutes, filtering and washed as above, affording 0.53 g which is characterized by thin layer HPLC analysis.

EXAMPLE 11

Cyclo (D-Trp-Cbz-Lyz-Val-Phe-N-Me-Ala-Tyr)

43 mg of the protected linear hexapeptide of Example 11 is dissolved in 6 ml of degassed dimethylformamide and cooled to −20° C. 0.0076 ml of DIPEA is added followed by 0.0095 ml of DPPA which resulted in a pH of about 7.4. The reaction mixture is maintained at this temperature overnight and an additional 0.0095 ml of DPPA is added and the pH adjusted to 7.6 with DIPEA. The reaction mixture is warmed to 0° C. after 2 days and maintained at this temperature for an additional 4 days. The solvent is evaporated to dryness in vacuo and water is added to the residue. The resulting precipitate is centrifuged and the water decanted. The solid material is dried in vacuo affording 0.0376 grams of Cyclo(D-Trp-Cbz-Lys-Val-Phe-N-Me-Ala-Tyr).

EXAMPLE 12

Cyclo(D-Trp-Cbz-Lys-Val-Phe-N-Me-Ala-Tyr)

Following the procedure of Example 12 however using SDPP in place of DPPA, there is obtained 0.036 grams of Cyclo (D-Trp-Cbz-Lys-Val-Phe-N-Me-Ala-Tyr).

EXAMPLE 13

Cyclo (D-Trp-Cbz-Lys-Val-Phe-N-Me-Ala-Tyr)

3.5 G of the hydrochloride salt of H-D-Trp-Cbz-Lys-Val-Phe-N-Me-Ala-Tyr-OH (3.5085 mmoles) is dissolved in 437.5 ml of degassed dimethylformamide resulting in a pH of about 5. The mixture is cooled in an ice bath and placed under a stream of nitrogen. 0.832 Ml of DPPA is added rapidly dropwise followed by 1.6735 g of sodium bicarbonate added in one portion. No changes in temperature are noted following either addition. The reaction is stirred at 0° C. for 67 hours. 115 Ml of mixed bed resin is added as stirring is continued for 5 hours. The reaction is filtered, and the solid material is washed and slurried three times with 40 ml of 80% DMF. The filtrate and washes are combined and evaporated to dryness in vacuo at 40° C. 100 Ml of water is added to the solid, the mixture allowed to stand overnight at 0° C., filtered, rinsed and slurried three times with 25 ml of water. The solid is dried affording 3.15 g of Cyclo (D-Trp-Cbz-Lys-Val-Phe-N-Me-Ala-Tyr).

EXAMPLE 14

Cyclo (D-Trp-Lys-Val-Phe-N-Me-Ala-Tyr)

A dry mixture of 20.3 mg of the product of Example 12 or 13 and 4.4 mg of 10% palladium on carbon are combined with 1.5 ml of a 5:95 mixture on a volume basis of 88% formic acid and methanol. The mixture is stirred for 2 hours and filtered through Celite which had been prewashed with 5% formic acid and methanol followed by washing with two 1 ml portions of methanol. The filtrate is freeze-dried affording a residue of 17 mg of "Cyclo(D-Trp-Lys-Val-Phe-N-Me-Ala-Tyr)."

The foregoing reaction was repeated using 10.8 mg and 20.9 mg respectively of the catalyst and affording similar quantities of the product.

What is claimed is:

1. A process for the preparation of Cyclo(D-Trp-Lys-Val-Phe-N-Me-Ala-Tyr) which comprises cyclizing at a molar concentration of from 0.5 to 0.001, in a solvent system consisting of N,N-dimethylformamide, dimethylsulfoxide, or mixtures thereof, the following linear peptide which may optionally be protected by one or more blocking groups:
H-D-Trp-Lys-Val-Phe-N-Me-Ala-Tyr-OH
wherein the reaction is carried out in the presence of a tertiary amine or sodium bicarbonate and diphenylphosphorylazide as a cyclizing agent at from −30° to +5° C. over a period of from 1 to 50 hours.

2. The process of claim 1 wherein the reaction is carried out at a molar concentration of about 0.008.

3. The process of claim 1 wherein the tertiary amine is triethylamine.

4. The process of claim 1 wherein the inorganic base is sodium bicarbonate.

* * * * *